United States Patent
Spaeth et al.

(10) Patent No.: US 7,340,316 B2
(45) Date of Patent: Mar. 4, 2008

(54) SYSTEM AND METHOD FOR PRODUCING MEDICAL DEVICES

(75) Inventors: John P. Spaeth, St. Louis, MO (US); Thomas F. Kirk, Ponte Vedra Beach, FL (US); Stacey Whiteside, Tempe, AZ (US)

(73) Assignee: Hanger Orthopedic Group, Inc., Bethesda, MD (US)

( * ) Notice: Subject to any disclaimer, the term of this patent is extended or adjusted under 35 U.S.C. 154(b) by 0 days.

(21) Appl. No.: 10/879,653

(22) Filed: Jun. 28, 2004

(65) Prior Publication Data

US 2005/0288809 A1  Dec. 29, 2005

(51) Int. Cl.
*G06F 19/00* (2006.01)

(52) U.S. Cl. ........................................ 700/98; 700/182

(58) Field of Classification Search ................. 700/98, 700/97, 118, 182; 345/418–420, 425, 427, 345/441; 382/128
See application file for complete search history.

(56) References Cited

U.S. PATENT DOCUMENTS

| | | | |
|---|---|---|---|
| 5,634,064 A | 5/1997 | Warnock et al. | |
| 5,737,599 A | 4/1998 | Rowe et al. | |
| 5,764,987 A | 6/1998 | Eidt et al. | |
| 5,781,652 A | 7/1998 | Pratt | |
| 5,781,785 A | 7/1998 | Rowe et al. | |
| 5,819,062 A | 10/1998 | Srikantappa | |
| 5,819,301 A | 10/1998 | Rowe et al. | |
| 5,969,822 A * | 10/1999 | Fright et al. | 356/608 |
| 6,016,491 A | 1/2000 | Kou | |
| 6,028,583 A | 2/2000 | Hamburg | |
| 6,144,386 A | 11/2000 | Pratt | |
| 6,289,364 B1 | 9/2001 | Borg et al. | |
| 6,421,460 B1 | 7/2002 | Hamburg | |
| 6,463,351 B1 * | 10/2002 | Clynch | 700/163 |
| 6,567,828 B2 | 5/2003 | Inohara et al. | |
| 6,772,026 B2 * | 8/2004 | Bradbury et al. | 700/98 |
| 6,792,370 B2 * | 9/2004 | Satoh et al. | 702/95 |
| 7,013,191 B2 * | 3/2006 | Rubbert et al. | 700/98 |
| 2002/0007294 A1 * | 1/2002 | Bradbury et al. | 705/7 |
| 2004/0068337 A1 * | 4/2004 | Watson et al. | 700/98 |
| 2006/0235877 A1 * | 10/2006 | Richard et al. | 707/104.1 |

FOREIGN PATENT DOCUMENTS

| | | |
|---|---|---|
| EP | 0 967 942 B1 | 6/2003 |
| WO | WO 98/30176 | 7/1998 |

OTHER PUBLICATIONS

International Search Report in International Patent Application No. PCT/US2005/22964, mailed Oct. 2, 2006.

* cited by examiner

*Primary Examiner*—Zoila Cabrera
(74) *Attorney, Agent, or Firm*—Stroock & Stroock & Lavan LLP

(57) ABSTRACT

The present invention relates generally to a method and system used to capture three-dimensional images for the purposes of, but not limited to, designing and fabricating medical devices and other medical-related uses of three-dimensional images. The present system generally includes a three dimensional digitizing system, direct conversion Computer Aided Design (CAD) software, a Central Fabrication Network (CFN) comprising of a Central Fabrication Center (CFC) and/or at least one other fabrication center, and preferably a network communicatively connecting at least one practitioner to a Central Design Center (CDC). Additionally, the present invention may include certain design protocols as well as training/education for its practitioners.

33 Claims, 6 Drawing Sheets

SYSTEM AND METHOD FOR PRODUCING MEDICAL DEVICES

BACKGROUND OF THE INVENTION

1. Field of the Invention

The present invention relates to a system and method of producing medical devices, such as Orthotic and Prosthetic devices, soft good garments and compression hose, facial masks, custom footwear, foot Orthotics and/or other custom goods or devices or volumetric comparisons, and in particular, a system and method of accurately producing medical devices.

2. Description of the Related Art

One of the primary goals in the manufacture of certain medical devices, such as orthotic and prosthetic structures, is to achieve a comfortable and accurate fit for the patient. In order to accomplish this, it is necessary to identify and define the precise shape of the patient's body part to be supported. For example, determining the precise shape of the body part is necessary for the formation of an effective mold, model, or mating part, such as the support socket of a clinical support device. Unfortunately, one cannot necessarily create a device such as an orthotic or prosthetic structure based solely on the shape of the body part to be supported. For example, in the case of an orthotic or prosthetic device, the support device is generally adapted to be fitted over a patient's limb in order to act as either a replacement for the missing limb or a support in the case of a pathogenic limb. This creates a substantial amount of constant pressure being exerted on the limb. However, most portions of the human body are not capable of withstanding constant, focused pressure for extended periods of time. As such, it is necessary to design the support socket in such a manner as to spread the pressure out in order to avoid concentrating pressure on any one portion of the limb. Thus, designing a comfortable and accurate medical device such as this requires a trained practitioner with knowledge of the various sensitivities of patients' body parts, such as a physician, a prosthetist or an orthotist, to make these necessary adjustments.

Currently, the most common way of defining the shape of a body part is by making a mold of the body part by hand. A trained practitioner can then manipulate the mold in order to correctly spread out the pressure to be exerted on the patient. The final shape is then cut by a milling or carving machine so as to form the physical model into a foam or plaster blank. This final foam or plaster shape is then draped in some manner with heated plaster or laminate to create the finished medical support device to be used on the patient. However, this method is prone to deviations caused by human error. Thus, in order to achieve an accurate fit by making a mold by hand, even a highly trained practitioner usually has to make multiple revisions requiring multiple moldings. This is extremely time-consuming and inefficient. Additionally, this method can be very limited in its accuracy.

Another known method of defining the shape of a body part is described by a family of patents by Pratt; including U.S. Pat. Nos. 5,781,652, 6,144,386 and 6,236,743. These patents describe a digitizing system that includes a probe that is placed in contact with the body part to be supported. The probe is structured to provide specific six-degree of freedom position and orientation information relative to a reference element. The position and orientation of the probe relative to the reference element is determined and the volume relative to the reference element through which the probe is passed is determined and stored by the digitizing system so as to determine the shape of a support area of the medical device which engages the body part to be supported. Although this method is faster than molding, it has numerous drawbacks. For instance, when the probe is in contact with a body part, the body part is slightly depressed which can result in inaccurate measurements. Further, similar to the currently known laser scanning methods described in more detail below, this method cannot be used to carve molds of body parts that contain more than one axis. Also, these devices cannot be used when the patient is moving.

Another known method of defining the shape of a body part is by utilizing a laser scanning device. These devices use laser refraction and reflectivity to map out the body part's precise shape and contour. The shape of the body part is then displayed onto a computer screen and can be manipulated using Computer Aided Design ("CAD") software. This information is then utilized by Computer Aided Manufacturing ("CAM") software which enables a carving machine to carve an accurate mold of the body part with the practitioner's adjustments. Although this method is more precise than molding by hand, existing systems have many drawbacks. For instance, many prior art systems are only able to track the movement of either the patient or the scanning device. Thus, either patient movement or movement of the scanning device can result in inaccurate scans. Additionally, the amount of information that is necessary to create a shape capable of manipulation by CAD software is relatively large. As such, CAD programs for use in these systems generally must be adapted to accept "high algorithm" software. However, CAM programs are generally "low algorithm" software, as carving machines can only process a relatively small amount of information compared with CAD programs. Thus, typical CAM software cannot accept the high algorithm CAD data necessary to achieve successful molding. Also, although there currently exists CAM programs that are capable of carving multiple axis molds, prior art CAM programs have been unable to utilize scanned images of body parts that contain more than one axis (e.g., an ankle and a foot) for carving. Currently, the CAM programs that can carve molds of multiple axes can only utilize templates of body parts, not actual scanned images. Thus, prior art CAM programs have not been able to achieve precise carving of the images having more than one axis that have been scanned and imported into the CAD program.

There are many additional known methods of defining a body part. For example, U.S. Pat. No. 6,463,351 issued to Clynch describes a method wherein a mold is made of the body part by hand, the mold in then sent to a central fabrication facility which scans the mold by a laser scanning device. The image created by the scanning device is then manipulated to provide the needed areas of build-up and relief. A carving machine to carve the device then utilizes this information. In addition to being incapable of carving actual images of body parts containing more than one axis, this method also has many additional drawbacks. For instance, the practitioner making the initial mold must send that mold to a central facility to be scanned. This can be cumbersome and inefficient. Additionally, the actual body part is not scanned, but rather only an initial mold of the body part is scanned. Such an approach can be prone to human error. Further, only the outside of the initial mold is scanned, which never touches the body part. Thus, any carving from a scanned image of the outside of the mold is at best an educated guess of the actual shape and contours of the body part.

The present invention is directed at a system and method of producing medical devices that overcome shortcomings of the prior art methods.

SUMMARY OF THE INVENTION

The present invention relates to a method and system used to capture three-dimensional images for the purposes of, but not limited to, designing and fabricating medical devices and other medical-related uses of three-dimensional images. The present system generally includes a three dimensional digitizing system, direct conversion Computer Aided Design (CAD) software, a Central Fabrication Network (CFN) comprising of a Central Fabrication Center (CFC) and/or at least one other fabrication center, and a network communicatively connecting at least one practitioner to a Central Design Center (CDC). Additionally, the present invention may include certain design protocols as well as training/education for its practitioners.

In general terms, the system begins with the three-dimensional digitizing system. The three dimensional digitizing system preferably comprises a direct scanning laser wand and a two-channel motion-tracking system. A practitioner, such as a physician, a prosthetist or an orthotist, scans the patient's body part to be supported, stabilized, braced or replaced with the laser scanning wand. The digitizing system generates an image of the body part that can be displayed on a computer monitor. Additionally, the wand can be used to add landmarks to the surface of the shape to further define its topography. This image, after undergoing the necessary modifications to be discussed below, will ultimately serve as the basis for which a mold for the medical device is generated.

The practitioner can manipulate the image of the body part, which ultimately changes the shape of the resulting mold; by using CAD software in order to avoid any sensitive areas on the patient and the pain and/or discomfort that can arise if the medical device exerts pressure on sensitive areas. Alternatively, the practitioner can send the data file that contains the scanned image information to the CDC, which is staffed by trained personnel who are capable of performing the necessary modifications.

After the modifications are performed, the image data file is then sent to a fabrication center, which can be the CFC or any other fabrication center. The fabrication center then manufactures the mold using the image data file. This results in an accurately fitting mold, because it is manufactured directly from the image of the actual patient's body part.

Additionally, the present invention contains CAD software that can join several complex shapes together making one contiguous shape. This is required for manipulating images of body parts that, for example, incorporate a 90-degree angle, such as an ankle or a shoulder. Further, the CAD software allows the practitioner to save the image data file, even files that contain images of body parts that incorporate 90-degree angles, in a file format that is readable by the carving machine. This allows the carving machine to carve a mold of the body part using an image of the patient's actual body part, even if that body part incorporates a 90-degree angle.

It is an object of the invention to provide a faster, cleaner, and less invasive alternative to traditional plaster casting.

It is a further object of the invention to provide an accurately fitting medical device.

It is a further object of the invention to use an image of a patient's actual body part in making a mold for a medical device, even if that body part incorporates a 90-degree angle.

It is a further object of the invention to have data files of images that are easily transferable and storable. This makes possible a permanent patient record that allows for rapid refitting and adjustments, the justification of medical necessity for a new device, and the sharing of patient information with the referring physician, allied health professional, managed care organization, and/or insurance company.

It is a further object of the invention to reduce the pain and possible trauma often associated with manipulating post-surgical spinal patients.

DETAILED DESCRIPTION OF THE PREFERRED EMBODIMENT

Figure 1:
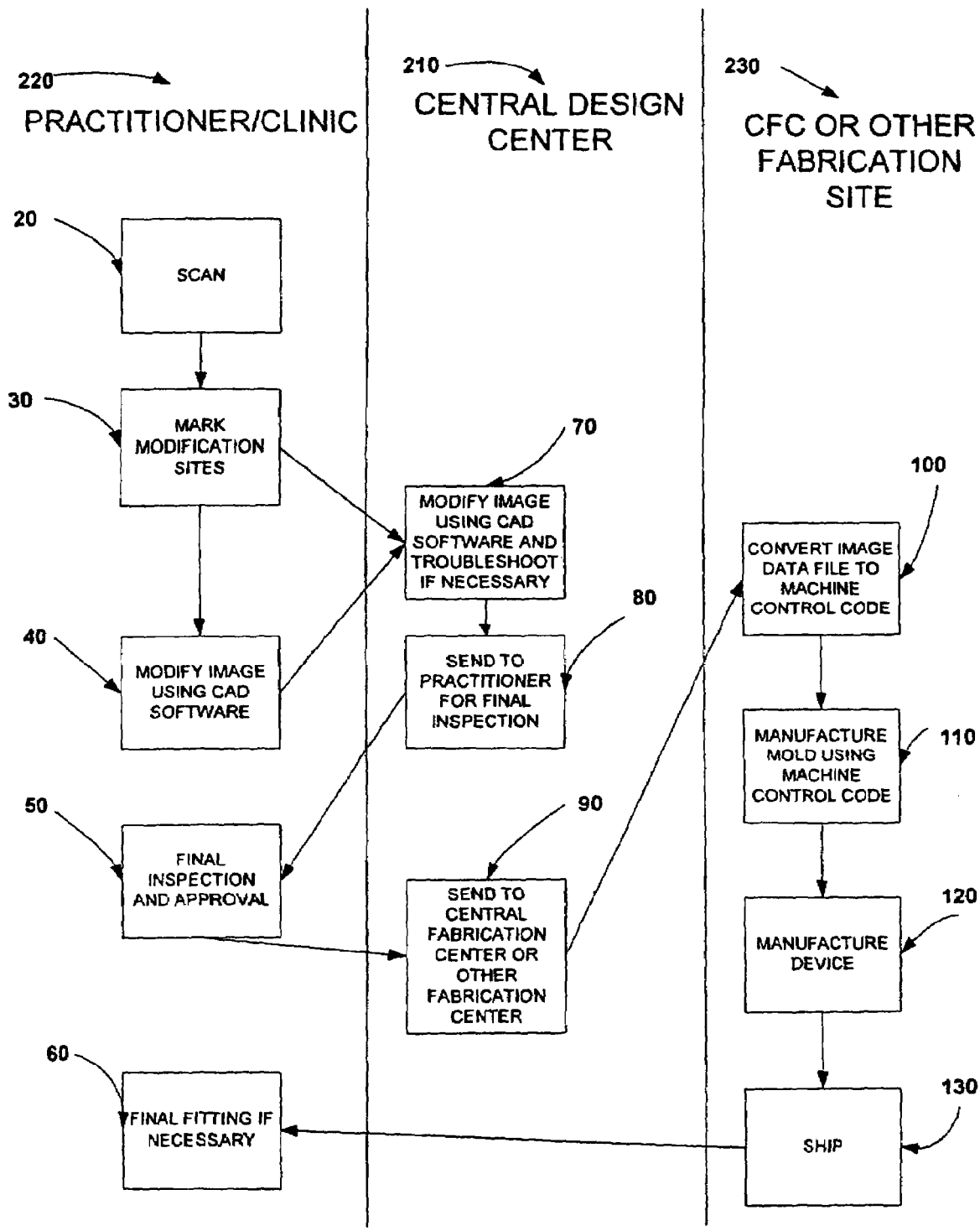
FIG. 1 is a flowchart depicting the system and the sequence of events, generally.

As shown in the drawings, the present invention is directed towards a method and system used to capture three-dimensional images for the purpose of designing and fabricating medical devices. In a preferred embodiment, the system comprises a three dimensional digitizing system used to capture images of body parts, and add optical stylus landmarks, for the purpose of custom Orthotic and Prosthetic devices, soft good garments and compression hose, facial masks and/or other custom or volumetric comparison devices. The system preferably comprises digital data acquisition technology including a three dimensional direct scanning laser wand with optical stylus/shutter mode and a two-channel motion-tracking device, a central design center, direct conversion CAD software, design protocols, a central fabrications network and training/education for its practitioners. The system is especially useful in configuring the support area or support socket of a medical device that comes in contact with the patient. Additionally, a preferred embodiment is especially suited for the design of devices to be used on multi-axis body parts.

Figure 2:
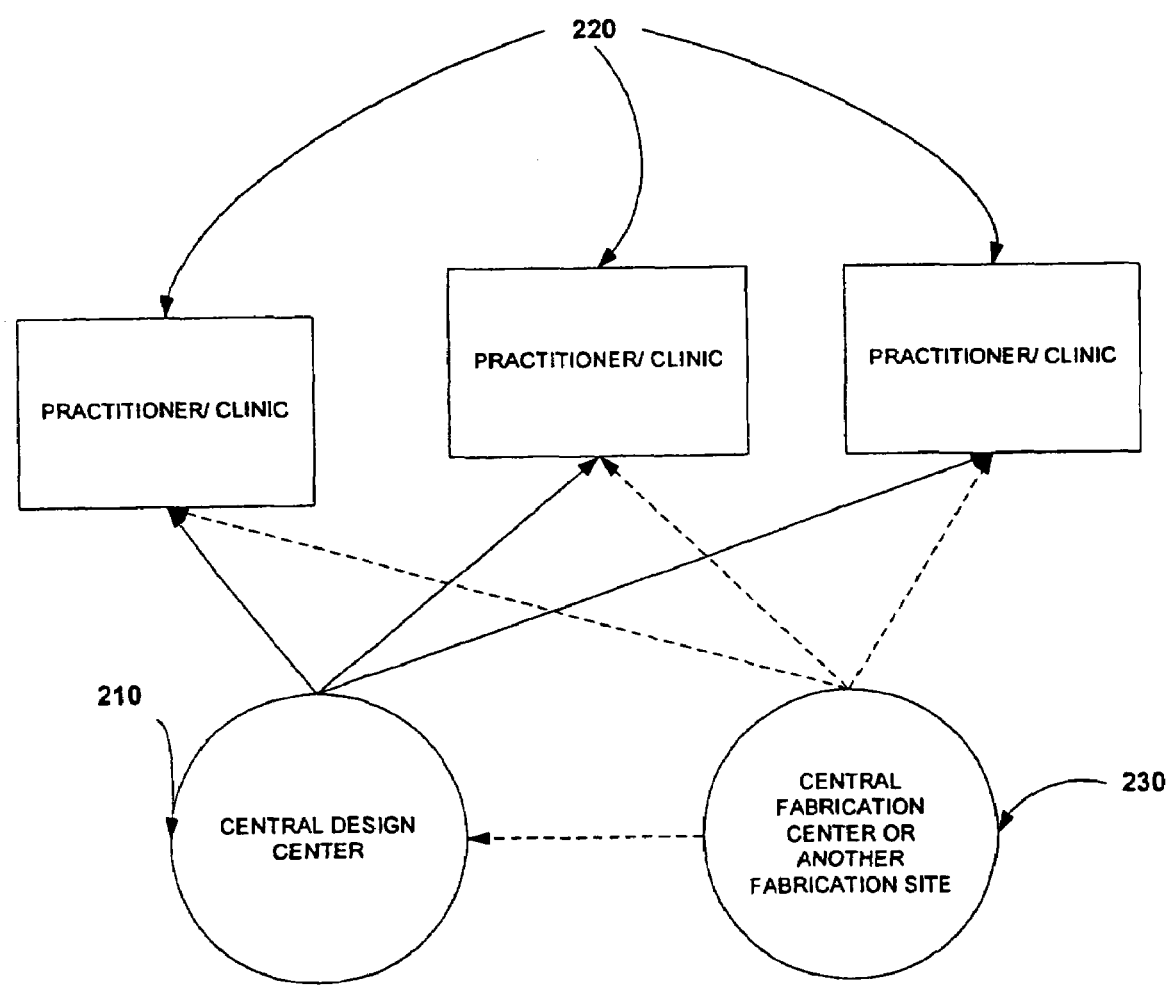
FIG. 2 depicts generally the relationship between the basic components of the system.

In general terms, as seen in FIGS. 1 and 2, the system begins with a practitioner, such as a physician, a prosthetist or an orthotist, scanning the patient's body part to be supported with a laser scanning device. The device is connected to a computer that contains CAD software that is capable of manipulating the scanned image. When scanning the body part, the practitioner preferably marks known points on the patient's body with the laser device in order to aid modification of the medical device at a later date. Preferably, the practitioner can mark these points by using the Optical Stylus, which is discussed in more detail below. The marks enable the practitioner to manipulate the medical device using the CAD software in order to avoid any sensitive areas on the patient and the pain and/or discomfort that can arise if the medical device exerts constant pressure on sensitive areas. Alternatively, the practitioner can send the data file that contains the scanned image information to a Central Design Center (CDC). The CDC is preferably staffed by personnel that are experienced in the areas of CAD software as well as orthotic or prosthetic design. The personnel at the CDC can use the marks to modify the image in order to achieve the most accurate and comfortable fit. Additionally, the CDC can use field input from practitioner preferences and/or templates to perform the modifications.

Once the practitioner modifies the image if he so chooses, he preferably sends the data file containing the modifications to the CDC. After the CDC receives the data file with modifications or after the CDC does the modifications, the CDC will then troubleshoot to ensure that the file contains no errors. After troubleshooting, the CDC sends the image date file with or without modifications to either the a Central Fabrication Center (CFC), another fabrication site of the practitioner's choosing, or back to the practitioner if he performs his own fabrications.

The CFC or another site that performs the fabrications then converts the image data file into machine control code so that the carving machine can cut the physical model into a foam or plaster blank, and/or perform other Computer Numeric Control (CNC) operations, such as drilling, trimming, buffing, etc. This final foam or plaster shape is then draped in some manner with heated plaster or laminate to create the finished medical support device to be used on the patient. The medical device is then shipped to the practitioner for final fitting, if necessary.

Figure 3:
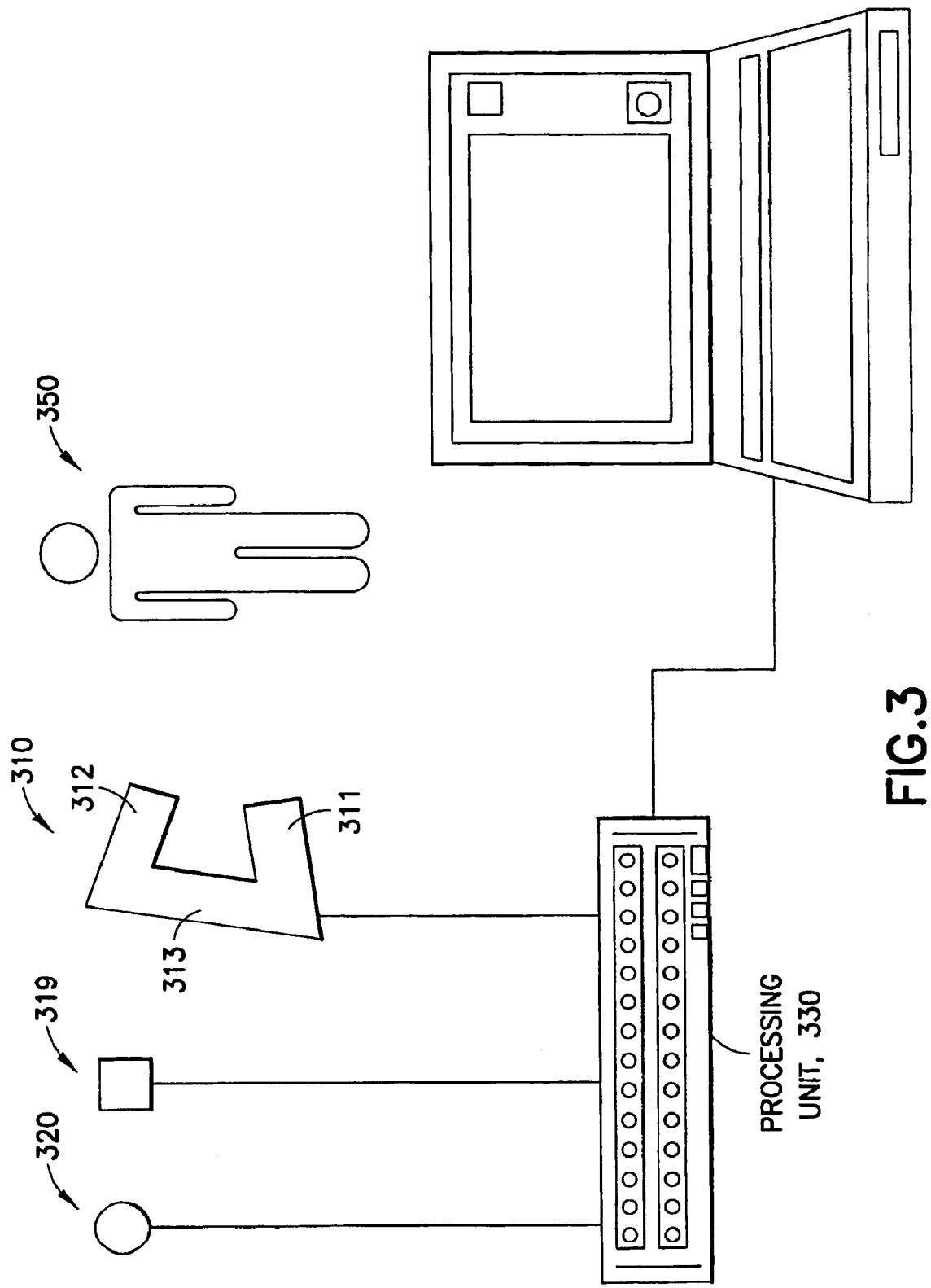
FIG. 3 depicts a preferred digitizing system.

Turning more specifically to the preferred digitizing system of the present invention, as depicted in FIG. 3, the digitizing system preferably includes a laser wand 310 which is a hand-held portable device that utilizes an integrated digital camera 311 and laser light source 312, and an electromagnetic receiver, which comprises a two-way tracking system. In order to use the digitizing system 300, the practitioner 220 first establishes the hemisphere of operation when the software initializes and then fans the laser light directly over the body part being scanned 350. In order to establish the hemisphere of operation, the practitioner first places the reference receiver 320 on the body part 350 in a manner as to avoid excessive movement of the receiver 320 relative to the body part being scanned 350. The two-channel tracking capability of the reference receiver 320 is able to track both the patient position and the position of the scanning device 310 relative to the patient's position 350. This capability is unique because it allows for patient movement while the practitioner is performing the scan. Unlike other prior art laser scanners, which require either the patient or the scanner to be fixed, the digitizing system of the present embodiment requires no fixation and un-encumbers both the scanning device and the patient during the scan. The ability to track and adjust for patient movement allows the practitioner to directly scan the patient without first having to take a cast, and then scan the cast (as described by Clynch). An exemplary example of a preferred digitizing system for use in connection with the present invention is the Polhemus FastSCAN™ laser scanner manufactured by Applied Research Associates of New Zealand (A.R.A.N.Z.), and, more particularly, the FastSCAN™ Cobra.

Figure 4:
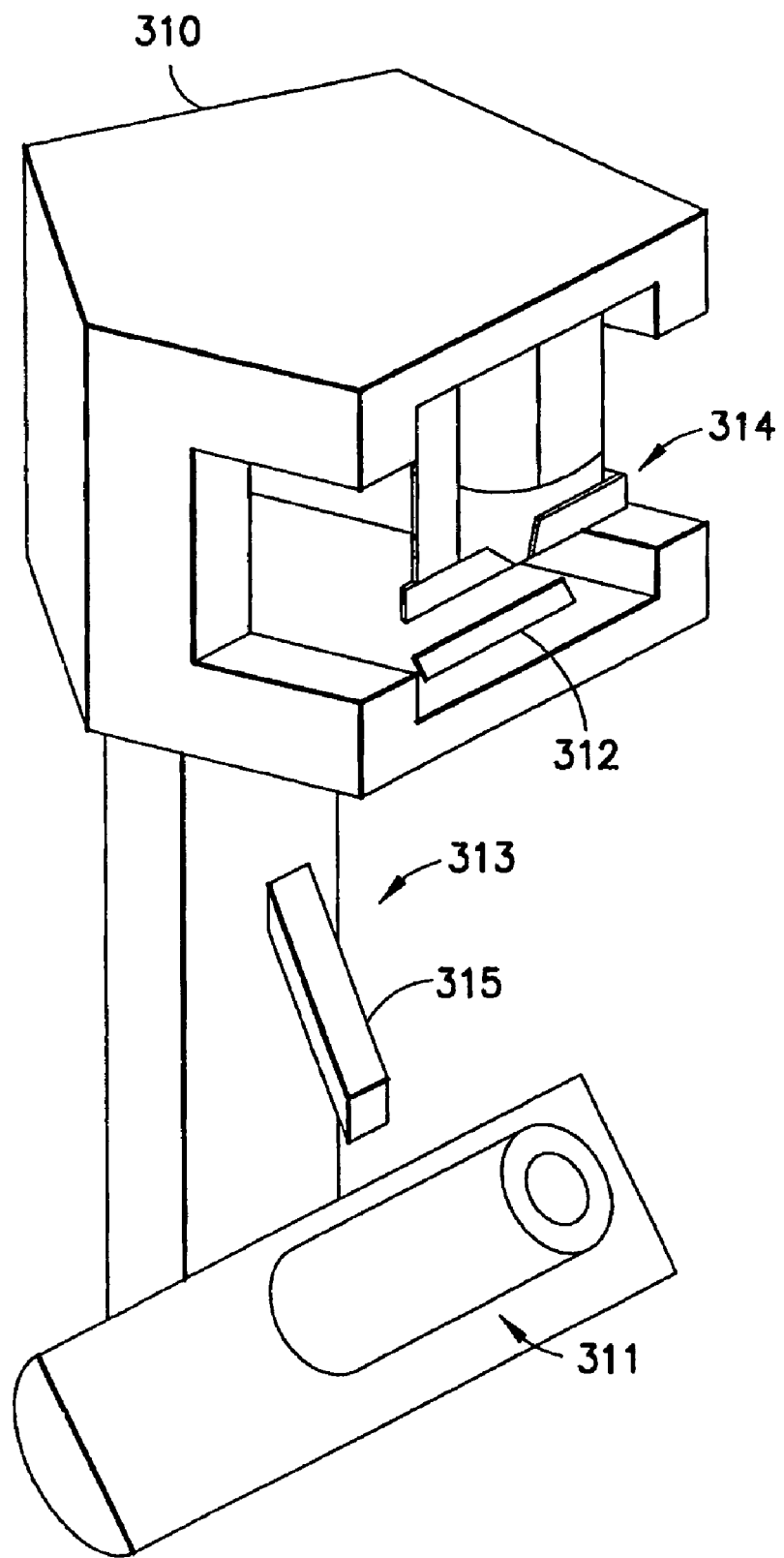
FIG. 4 depicts a preferred laser scanner.

FIG. 4 depicts a preferred laser wand 310. In use, the refracted light from the laser light source 312 is picked up and filtered by the digital camera 311, and interpreted by the computer software as a shape. After successive passes of the wand 310 fanning light over the entire surface under scan, the software begins to build a three-dimensional image of the body under scan. The purpose of this scan is to substitute for the conventional method of casting the body part in plaster and then either digitizing or manually molding the resultant plaster model. By scanning the body directly, the image undergoes less distortion and more accurately represents the actual shape and dimension of the body part under scan. In many instances, the plaster procedure can be time consuming and uncomfortable, and at times painful, especially when trauma cases are being treated. At all times the plaster casting procedure is messy and unsanitary. By direct scanning the patient, he/she is subjected to fewer traumas through having to endure the casing procedure.

Turning specifically to the exemplary laser scanner 310, it comprises a non-contact range finder based on projection and simultaneous detection of laser light, coupled with a means of tracking the position and orientation of the range finder as it is scanned over the body's surface. In the FastSCAN™ Cobra, the presently preferred laser scanner, the range finding optics are contained in the handheld "Wand," 310 and the tracking is done with a Polhemus FASTRAK® magnetic tracker. Both the video processing and tracker electronics are contained in the Processing Unit ("PU") 330.

As shown in FIG. 4, the exemplary Wand 310 consists of a centrally mounted laser light source 312 and a miniature digital camera 311. The practitioner points the Wand 310 at the body part (not shown), and the camera 311 on the Wand 310 records the intersection of the laser line generated by the laser light source 312 and the object, i.e. a profile. The three dimensional location of the profile with respect to the Wand 310 is computed using triangulation. The operator scans the complete object by sweeping the Wand 310 over different parts of the surface, collecting many profiles grouped into several sweeps. The Wand 310 preferably has two controls (e.g., trigger and sensitivity controls), and four status indicators (power, laser, scan, and a sensitivity bar graph). In a preferred embodiment, the sensitivity control and all status indicators are located on the control panel, located on the rear of the Wand 310, and the trigger is located on the underside of the handgrip 313.

In the exemplary embodiment, the PU 330 houses the electronics for the magnetic tracker and the video processing electronics. The PU 330 has connections for the Wand 310 (video and receiver connection), the Transmitter 315, the Reference Receiver 320, ECP parallel port (computer interface) and power. One receiver mounted in the Wand 310 allows the PU 330 to determine the position and orientation of the Wand 310 at all times, and hence locates each profile relative to the Transmitter 315, which generates a magnetic field in three dimensions. The amplitude of the magnetic field the Transmitter 315 generates determines the position and orientation of each receiver. Similarly, by placing the Reference Receiver 320 on the object 350, and selecting it to be the reference device, the computer can locate each profile relative to the body part. This makes it possible to move the body part during scanning. It should also be noted that in one embodiment, the Transmitter 315 is contained within the Wand 310.

Turning now to the central design center (CDC) 210 in the exemplary embodiment, as seen generally in FIG. 1, the preferred embodiment comprises a staff with expertise in CAD and CAM software. At least one of the practitioners 220 is preferably connected, electronically, telephonically or by other means, to the CDC 210. After the practitioner scans the patient 20, and perhaps after modifying the image using CAD software 40, the three-dimensional image is sent, preferably electronically (perhaps by way of email), to the CDC 210. This can be done within a matter of minutes from the time the practitioner 220 initially scans 20 the patient.

The staff at the CDC 210 can then evaluate the image and make any modifications 70 as required. After modification, the image is then transferred 80, preferably electronically, back to the practitioner 220 for inspection and final approval 50. In an alternative embodiment, the practitioners can modify their own images 40 and consult with the CDC staff. The CDC 210 then preferably routes the finished design 90 to either the central fabrication center (CFC) 230, to another fabrication center 230 that is part of the central fabrication network (CFN) 10, or a fabrication center of the practitioner's choosing 230. In an exemplary embodiment, the CDC 210 routes the image 90 to the best fabrication facility for its production. Preferably, the CDC 210 has multiple designers who check the images for accuracy and completeness before routing them for production. In an exemplary embodiment, the CDC 210 also provides permanent storage of the images for subsequent recall. These images can be useful to determine the transformation of a patient's dimensions indicating the progress or changes in their physical condition over time. In an exemplary embodiment, all the practitioners 220 are connected to the CDC 210 through a network such as a secure intranet and thus have access to each other for consultation and collaboration. This ability has the potential to sum the total experience and ability of all the practitioners as well as the CDC personnel and provide patients with exceptional depth of treatment and care. Additionally, the ability to route production work to a network of central fabrication centers, rather than a single production facility, means that production orders can be expedited. In an exemplary embodiment, the entire process can take just minutes from the time the patient's digital image is created and transmitted for fabrication.

Figure 5:
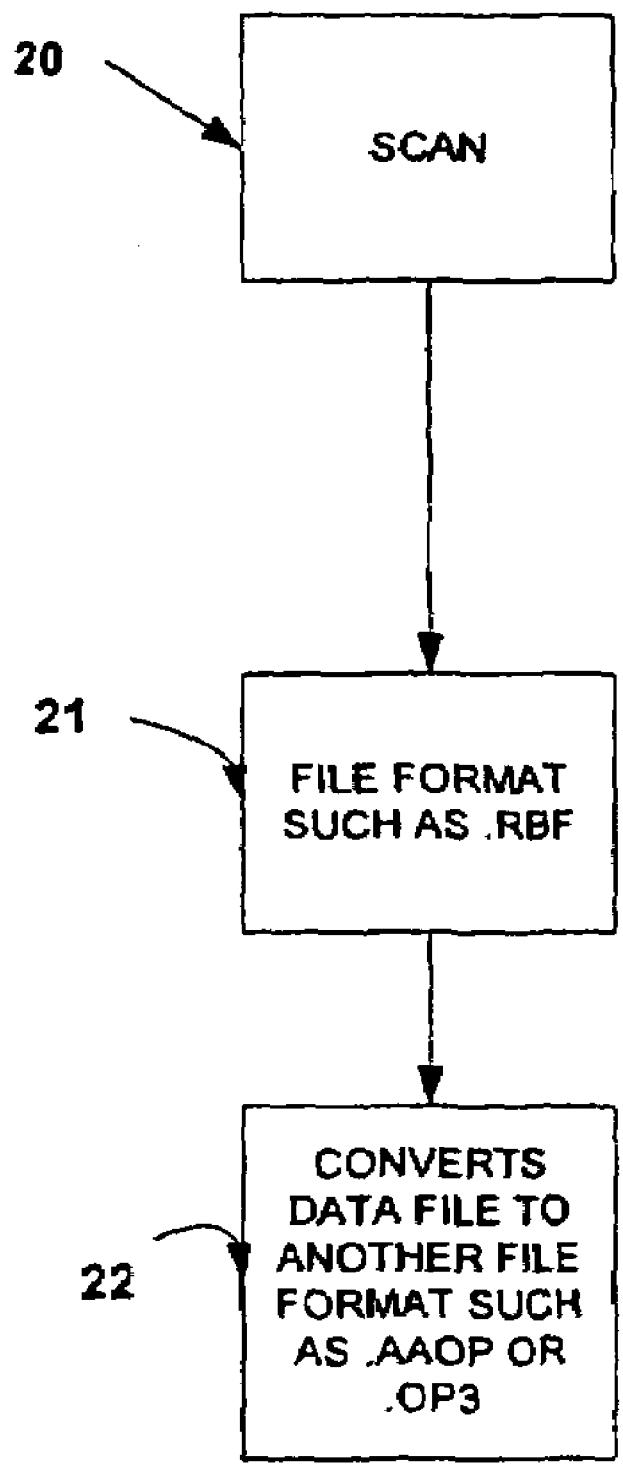
FIG. 5 depicts generally the events in a preferred file format conversion.

Turning now to the CAD software, as seen generally in FIG. 5, the exemplary embodiment is able to input a design directly from an iso-surfaced three-dimensional image (which is created by the digitizing system discussed above), which is an image that is made up of many smaller geometric shapes. Many prior art CAD application packages use the digital image merely as a reference, then use that reference to stretch or mold a predetermined shape template imbedded within the software to the same approximate dimension. This creates more of a facsimile of the image rather than an actual surfaced model of the original. An exemplary embodiment of the present invention imports the three-dimensional image directly from the scanning device, with a native surface that has been created by surfacing software, such as RBF surfacing software, as part of the laser scanner. That surfaced image is then imported into the CAD software for display and manipulation and/or modification.

The exemplary embodiment also contains an imbedded file conversion as part of the scanner's file output, as depicted in FIG. 5. When the body part is scanned 20, the generated image file is in particular file format 21, such as the .RBF file format. However, many CAD programs utilize different formats, such as the .AAOP file format. In an exemplary embodiment of the present invention, the scanner's file output contains file conversion software that enables the user to save the image in a format readable by the CAM software. This file conversion software can, for example, convert an .RBF file into an .AAOP file 22. Additionally, it can convert an .RBF file into a file that can also be used in a CAM program, such as Hanger Orthopedic Group Inc.'s ".OP3" file format 22.

A preferred embodiment of the CAD software uses open GL graphic language, which allows for direct access to the three-dimensional image's digital components for direct manipulation. Preferably, this allows for the chaining together of complex geometric shapes. An exemplary embodiment comprises a file format that allows the CAD program to operate in more than one axis. This is useful in scanning body parts that contains more than one axis, such as a leg, an ankle and a foot. A preferred embodiment file format, such as Hanger Orthopedic Group, Inc.'s ".OP3" file format, allows the image file to be translated for use in a CAM program. In the preferred embodiment, the image used in the CAD program is the actual image that was scanned. Thus, the preferred embodiment file format allows the actual image of the body part to be scanned in more than one axis, then allows the actual image of the body part to be capable of being translated from the high algorithm CAD program into the low algorithm CAM program, which enables the image to be carved in more than one axis. Preferably, a practitioner can scan a body part, make any necessary modifications, and then be able to save the file in a plurality of different file formats. Preferably, when the practitioner attempts to save the file, the CAD software prompts him to choose which format he would like the file to be saved as. This function enables the practitioner to save the file in a format that is directly readable by a CAM program. Thus, the practitioner can manipulate an image of a body part containing multiple axes, and save that image in a file format which is readable by CAM software and able to be carved by a carving machine. This is different from current systems, none of which have images of scanned multiple-axis objects saved onto a file format that is readable by CAM software and/or carvable by a carving machine.

Additionally, the preferred embodiment contains certain design protocols. Preferably, the laser wand 310 contains an Optical Stylus embedded therein. The Stylus may be activated by a flipping a switch 314 located on the scanner's laser line generator in order to converge the laser onto a point. In this or another embodiment, the trigger 315 on the laser scanner 310 comprises a function which allows the practitioner to save points created by the laser scanner 310 onto the image data file. Additionally, the practitioner 220 can save one or more lines created by holding down the trigger 315 while the laser is converged onto a point.

An additional design protocol which can be found in an exemplary embodiment is automatic scanner resolution based on the size of the scan. In this embodiment, the PU 330 adjusts the resolution value in accordance with the size of the scan. Higher resolution values reduce the number of points and facets. This results in a smaller file to be exported from the CAD program and subsequently results in faster rendering of exported scans when loaded into other programs. Lower resolution values produce larger, slower and more detailed mesh.

In an additional design protocol that can be found in a preferred embodiment, the PU 330 is communicatively coupled to one or more user stations 340 via any of a number of networks, such as a local area network, wide area network, the Internet, wireless network, satellite transmission, virtual private network and the like, utilizing essentially any type of communication protocol, such as Ethernet, IP addressing, transmission via data packets and the like. It is to be understood by those skilled in the art that this communication can be, but is not limited to, via a USB cable.

Figure 6:
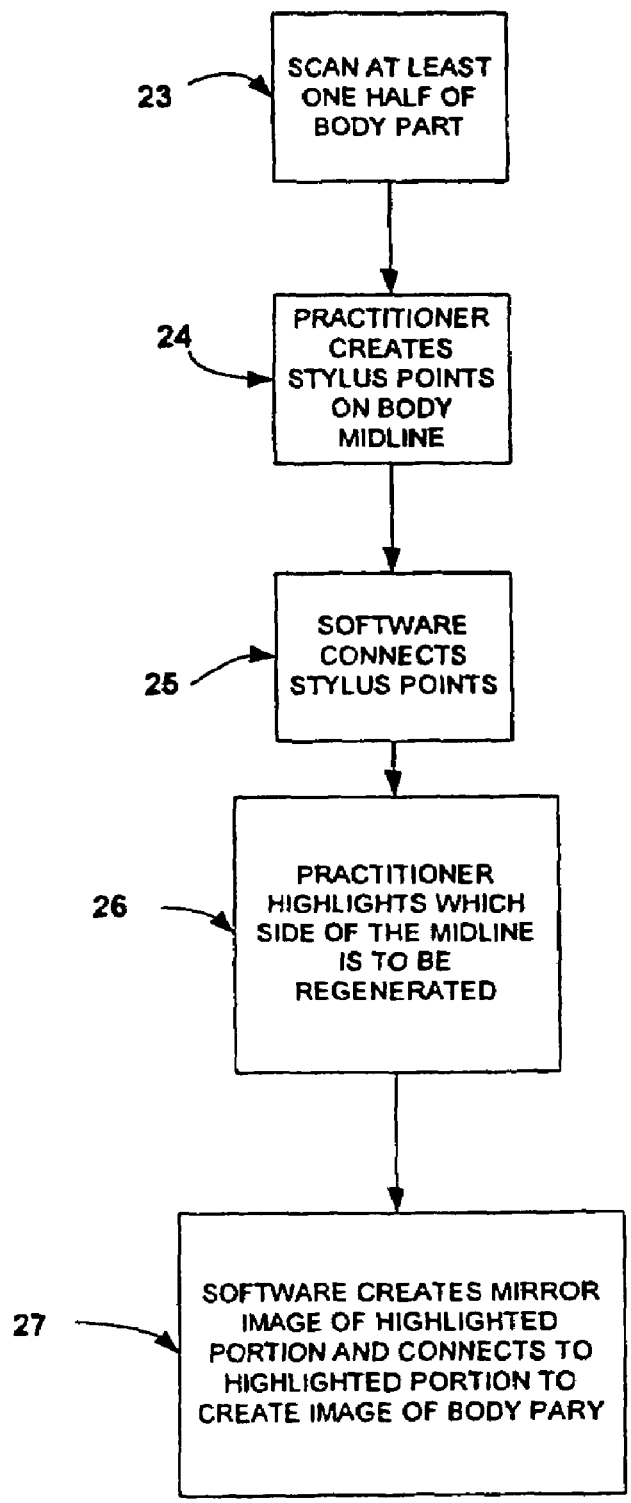
FIG. 6 depicts generally the events when utilizing the preferred symmetry-build software.

Additional protocols that can be found in other embodiments include attributes of the file format that allow for greater flexibility in scanning the patients. Because many patients that require medical devices have undergone or may still be undergoing trauma, manipulation of the patient 350 in order to achieve a scan can be difficult. For instance, a patient requiring a spinal jacket may have a back injury that prohibits a practitioner from moving the patient in order to achieve a scan of the entire torso to be fitted. Thus, as seen in FIG. 6, one embodiment of the CAD software allows the practitioner to scan one half of the body part to be supported 23, then generates a mirror image of the scanned body part 27 to be used as the half not scanned (called symmetry-build software). If the practitioner, using the Optical Stylus, saves points along the midline of a body part 24 to which a mirror image is going to be created of one half of the body part 27, the CAD software then connects these points into a line 25 and establishes the line as the midpoint of the body part. The data on the side of the line comprising the half to be regenerated, as designed by the practitioner highlighting the correct side 26, as the mirror image is then regenerated as a mirror image that begins on the line and continues opposite and adjacent to the scanned portion of the body part 27.

Another example of such design protocols includes inversion build software, which allows for the scanning of the inside of a small cylinder, such as a cast for a leg. This is achieved by splitting the cylinder in half and scanning the inside of each half of the cylinder as well as saving stylus points by way of the Optical Stylus. The CAD software then joins the halves together by connecting the stylus points of the two halves, and inverts by converting the inside surface into the outside surface. This image can then be manipulated by the practitioner who can then initiate the process of producing a mold. Prior art systems reproduce the outside of the cylinder, which can result in less accuracy and distortion of the surface topography.

Turning now to the Central Fabrication Network (CFN) 200 of the preferred embodiment, the CFN 200 comprises at least one fabrication site 230 that is connected to the CDC 210 and/or to at least one practitioner 220, preferably by electronic means. Because of the communication between the CFC 230 and the CDC 210 and/or at least one practitioner 220, the CFC 230 is able to produce a medical device within 24 hours of a patient's scan. The CFN's at least one fabrication site 230 contains CAM software that is capable of reading the file format used in the CAD software. This allows the at least one fabrication site to carve molds from the actual image of the body parts that are scanned. This further allows the at least one fabrication site to carve comprising of more than one axis from the actual images of the scanned body parts.

Turning now to the training/education component of the preferred embodiment, one of ordinary skill in the art would recognize that use of the digitizing equipment, the CAD software and the preferred system as a whole requires the practitioners to be trained. Thus, the preferred embodiment provides for training and education, preferably standardized, to at least one of the practitioners that takes part in the system. In an exemplary embodiment, at least one practitioner will be provided with clinical protocols for all business types serviced by the system and will receive hands-on training of the CAD software. Additionally, in the exemplary embodiment at least one practitioner will perform at least one scan (preferably various scans under various conditions) in order to simulate at least one patient care environment. In one embodiment, at least one practitioner is ensured core competency and then given the opportunity to scan at least one volunteer patient and/or carve check sockets and/or dynamically fit the socket to the at least one patient. In this or another embodiment, the at least one practitioner's scan and/or CAD modification and/or check socket fit is evaluated and critiqued.

What is claimed is:

1. A three dimensional digitizing system for designing external medical devices comprising:
   a direct scanning laser device for scanning an exterior of a patient's body part, said laser device comprising a digital camera, a laser light source and an electromagnetic receiver, said laser device being structured and disposed to produce a plurality of laser lines read by said laser device and being structured and disposed to create contour coordinates of the exterior of said body part, said laser device comprising a transmitter within the laser device designed to generate a three-dimensional magnetic field;
   a two-channel motion-tracking device designed to track the object's movement in relation to the laser device, said two-channel motion-tracking device comprising a reference receiver capable of tracking the body part's position and a position of the laser device relative to the body part; and
   a processing unit (PU), said processing unit comprising electronics for the two-channel motion-tracking device, video processing electronics and connections for the laser device, the reference receiver, the computer interface and a power source, and being structured and disposed to calculate a three-dimensional digital image of said body part by using data received by said laser device, said transmitter and said two-channel motion tracking device;
   wherein said laser device further includes an optical stylus to create a digital landmark on the contour coordinates, wherein the optical stylus has a first position at which the laser device creates contour coordinates of the exterior of said body part, the optical stylus having a second position at which the laser device focuses the laser light to create a digital landmark on the contour coordinates, said digital landmark comprising a plurality of data, consisting of multiple coordinates corresponding to a section of the patient's body part;
   wherein the system is capable of storing the digital landmark;
   wherein the digital image can be used to create an external medical device and the digital landmark can be used to modify the medical device to customize the external medical device.

2. The system as recited in claim 1, further comprising a network communicatively connecting at least one practitioner to a Central Design Center (CDC).

3. The system as recited in claim 1, wherein said laser device is capable of being moved with the laser light converged onto a point along the body part to provide a corresponding line in the three-dimensional digital image of the body part.

4. The system as recited in claim 1, wherein said laser device comprises at least one control and at least one status indicator.

5. The system as recited in claim 1, wherein the external medical device is an orthotic or prosthetic device.

6. The system as recited in claim 1, further comprising file conversion software capable of saving a scanned image in a format readable by either Computer Aided Manufacturing (CAM) software and/or Computer Aided Design (CAD) software.

7. The system as recited in claim 1, further comprising Computer Aided Design (CAD) software capable of directly inputting, modifying and saving said digital image in a file format, said file format capable of being readable by Computer Aided Manufacturing (CAM) software.

8. The system as recited in claim 7, wherein said digitizing system utilizes a file format that allows said CAD software to operate in more than one axis.

9. The system as recited in claim 7, wherein said CAD software utilizes an .OP3 file format.

10. The system as recited in claim 7, wherein said CAD software is capable of storing an image file in at least two different file formats.

11. The system as recited in claim 7, wherein said CAD software is capable of saving images of objects that contain multiple axes in a format that is readable by Computer Aided Manufacturing (CAM) software.

12. The system as recited in claim 1, wherein said PU comprises automatic scanner resolution software which is capable of adjusting the resolution value of said image.

13. The system as recited in claim 1, wherein said PU is communicatively coupled to at least one user station via a first network that utilizes a first communication protocol.

14. The system as recited in claim 13, wherein said first network is either a local area network, a wide area network, the Internet, a wireless network, satellite transmission, or a virtual private network.

15. The system as recited in claim 13, wherein said first communication protocol is either Ethernet, IP addressing or transmission via data packets.

16. The system as recited in claim 1, further comprising symmetry-build software.

17. The system as recited in claim 1, further comprising inversion-build software.

18. The system as recited in claim 1, further comprising a Central Fabrication Network (CFN) comprising at least one fabrication center communicatively connected to at least one practitioner.

19. The system as recited in claim 18, wherein the CFN is either a local area network, a wide area network, the Internet, a wireless network, satellite transmission, or a virtual private network.

20. The system as recited in claim 18, wherein the CFN uses a second communication protocol chosen from one of the following: (a) Ethernet, (b) IP addressing or (c) transmission via data packets.

21. The system as recited in claim 18, wherein said at least one fabrication center includes a Central Fabrication Center (CFC).

22. The method of claim 21, further comprising utilizing a two-channel motion-tracking device comprising a reference receiver capable of tracking said body part's position and the position of said laser scanning device relative to said body part.

23. The method of claim 21, further comprising utilizing a processing unit to create said data image file by using data received from said laser scanning device, said transmitter and said two-channel motion tracking device, said processing unit comprising electronics for said two-channel motion-tracking device, video processing electronics and connections for said laser scanning device, said reference receiver, a computer interface and a power source.

24. The method of claim 21, wherein selectively modifying the digital image proximate the digital landmark includes modifying the digital image so as to account for any sensitive areas of the body part.

25. The method of claim 21, further comprising saving the digital image in a format that is capable of being readable by Computer Aided Manufacturing (CAM) software.

26. A method of designing and fabricating molds for external medical devices, the method comprising:
creating a data image file of a patient's body part by:
scanning an exterior of said patient's body part with a direct scanning laser device, said direct scanning laser device comprising an integrated digital camera, a laser light source and an electromagnetic receiver, the laser device having an optical stylus, to create a digital landmark on the contour coordinates the optical stylus having a first position at which the laser device creates contour coordinates of the exterior of said body part, the optical stylus having a second position at which the laser device focuses laser light to create a digital landmark on the contour coordinates;
creating contour coordinates of the exterior of said body part utilizing the laser device, said laser device comprising a transmitter within the laser device for generating a three-dimensional magnetic field;
creating a digital landmark on the contour coordinates, said digital landmark comprising a plurality of data, consisting of multiple coordinates corresponding to a section of the patient's body part;
storing the digital landmark as a plurality of data, consisting of multiple coordinates;
creating a digital image and using the digital image to create a mold of an external medical device; and
selectively modifying the mold based on the digital landmark to customize the external medical device.

27. The method as recited in claim 26, further comprising sending the data image file to a Central Design Center (CDC).

28. The method as recited in claim 27, wherein modifying the data image file is performed at the CDC.

29. The method as recited in claim 26, wherein said method further comprises a Central Fabrication Network (CFN), said CFN comprising at least one fabrication center communicatively connected to at least one practitioner, and wherein said carving a mold is performed at said at least one fabrication center.

30. The method as recited in claim 29, wherein said CFN comprises a Central Fabrication Center (CFC), and wherein said carving a mold is performed at said CFC.

31. The system of claim 1, further comprising a computer interface, said computer interface being structured and disposed to display said digital image.

32. The system of claim 1, further comprising an instrument for producing a mold for a medical device, said mold being substantially similar to said digital image.

33. The system of claim 32, further comprising an instrument for producing an external medical device based substantially on said mold.

* * * * *